United States Patent
Hintze

(10) Patent No.: US 8,657,792 B1
(45) Date of Patent: Feb. 25, 2014

(54) MEDICINAL TUBE LUBRICATING SYSTEM AND ASSOCIATED USE THEREOF

(76) Inventor: Kathy Hintze, Baltimore, MD (US)

(*) Notice: Subject to any disclaimer, the term of this patent is extended or adjusted under 35 U.S.C. 154(b) by 43 days.

(21) Appl. No.: 13/337,655

(22) Filed: Dec. 27, 2011

Related U.S. Application Data

(60) Provisional application No. 61/490,954, filed on May 27, 2011.

(51) Int. Cl.
*A61M 5/32* (2006.01)
*A61M 5/00* (2006.01)

(52) U.S. Cl.
USPC .............................. 604/174; 604/172; 604/265

(58) Field of Classification Search
USPC .......................................... 604/172–174, 265
See application file for complete search history.

(56) References Cited

U.S. PATENT DOCUMENTS

| | | | | |
|---|---|---|---|---|
| 3,345,988 A | * | 10/1967 | Vitello | 604/172 |
| 3,598,127 A | * | 8/1971 | Wepsic | 604/265 |
| 4,666,111 A | | 5/1987 | Schuler | |
| 4,846,807 A | | 7/1989 | Safadago | |
| 4,950,232 A | * | 8/1990 | Ruzicka et al. | 604/43 |
| 5,810,781 A | | 9/1998 | Bierman | |

* cited by examiner

*Primary Examiner* — Nicholas Lucchesi
*Assistant Examiner* — Niyati D Shah

(57) ABSTRACT

A medicine delivering tube capable of transporting fluid from an existing medicine dispensing unit to the patient preferably includes a protective sleeve concentrically positioned about the medicine delivering tube such that a lubricant receiving zone is intercalated between an outer surface of the medicine delivering tube and an inner surface of the protective sleeve. The protective sleeve preferably includes a plurality of holes spaced along a major surface area of the protective sleeve. A lubricant dispensing unit is in fluid communication with the protective sleeve thereby injecting lubricant into the lubricant receiving zone for reducing friction between the outer surface of the medicine delivering tube and the inner surface of the protective sleeve. In this manner, upon applying an external force to the protective sleeve, the lubricant is caused to egress the protective sleeve via the holes thereby reducing friction along an outer surface of the protective sleeve.

1 Claim, 5 Drawing Sheets

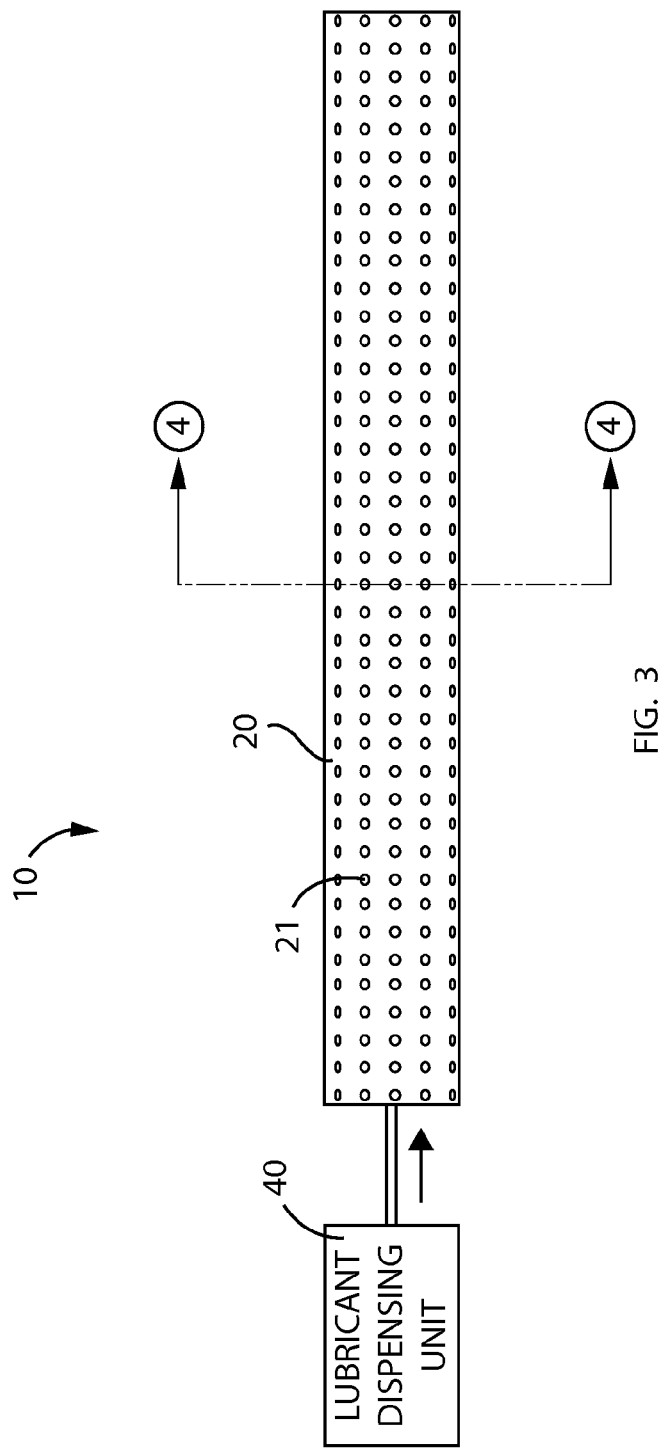

MEDICINAL TUBE LUBRICATING SYSTEM AND ASSOCIATED USE THEREOF

CROSS REFERENCE TO RELATED APPLICATIONS

This application claims the benefit of U.S. Provisional Application No. 61/490,954, filed May 27, 2011, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE DISCLOSURE
TECHNICAL FIELD

This disclosure relates to IV/NG tubes and, more particularly, to a lubricating system for preventing accidental and/or purposeful extraction of IV/NG tubes that deliver medicine and other contents to a patient.

PRIOR ART

In the medical field it is common practice to supply blood and other fluids to the patient intravenously or nasogastricly. Standard intravenous (IV/NG) supply devices include an intravenous catheter penetrating the skin and coupled to a supply tube. The supply tube is typically connected to a supply bag or pouch from which the contents are introduced to the patient by gravity. Alternatively, the supply tube may be connected to a standard infusion pump to provide a more accurate and controlled rate of flow through the IV/NG tube.

The standard supply tube is formed from a pliable, clear plastic material which is easily twisted and handled. However, the flexible nature of the tubing can result in the tubing becoming dislodged during use. The supply tubing is often used in lengths of four or more feet, depending on the patient, which can further result in the excess length of tubing becoming tangled and separated from the patient's body. The dislodging and/or snagging of the tube may not be observed for some time and can result in injury to the patient. That is, patients may accidentally or purposefully pull out their IV/NG tubes.

There is therefore a need for a system which is able to reduce the risks of dislodging an intravenous supply tube without interfering with the flow of fluids therein and thereby reduce the risk of accidental/purposeful dislodging of the IV/NG tube.

BRIEF SUMMARY OF THE DISCLOSURE

In view of the foregoing background, it is therefore an object of the non-limiting exemplary embodiments to provide a medicinal tube lubricating system for ensuring a patient continuously receives medication during an extended time period. These and other objects, features, and advantages of the disclosure are provided by a medicinal tube lubricating system including a medicine delivering tube capable of transporting fluid from an existing medicine dispensing unit to the patient, a protective sleeve concentrically positioned about an entire longitudinal length of the medicine delivering tube such that a lubricant receiving zone is intercalated between an outer surface of the medicine delivering tube and an inner surface of the protective sleeve. The protective sleeve preferably includes a plurality of holes spaced along a major surface area of the protective sleeve.

A lubricant dispensing unit is in fluid communication with the protective sleeve thereby injecting lubricant into the lubricant receiving zone for reducing friction between the outer surface of the medicine delivering tube and the inner surface of the protective sleeve. In this manner, upon applying an external force to the protective sleeve, the lubricant is caused to egress the protective sleeve via the holes thereby reducing friction along an outer surface of the protective sleeve.

In a non-limiting exemplary embodiment, the lubricant receiving zone continuously extends about an uninterrupted curvilinear path extending along an entire circumference of the outer surface of the medicine delivering tube.

In a non-limiting exemplary embodiment, the lubricant maintains continuous contact with the outer surface of the medicinal delivering tube and the inner surface of the protective sleeve prior to egressing from the holes.

In a non-limiting exemplary embodiment, the holes pass through an entire cross-section of the protective sleeve thereby extending from the lubricant receiving zone and terminating at the outer surface of the protective sleeve.

In a non-limiting exemplary embodiment, the lubricant simultaneously ingresses the lubricant receiving zone via one of the holes and egresses from remaining ones of the holes.

In a non-limiting exemplary embodiment, the lubricant is prohibited from entering an interior of the protective sleeve.

In a non-limiting exemplary embodiment, the holes are radially oriented and equidistantly spaced from a center of the medicine delivering tube.

The present disclosure further includes a method of utilizing a medicinal tube lubricating system for ensuring a patient continuously receives medication during an extended time period. Such a method preferably includes the chronological steps of: providing a medicine delivering tube and an existing medicine dispensing unit wherein the medicine delivering tube is capable of transporting fluid from the existing medicine dispensing unit to the patient; and providing and concentrically positioning a protective sleeve about an entire longitudinal length of the medicine delivering tube such that a lubricant receiving zone is formed between an outer surface of the medicine delivering tube and an inner surface of the protective sleeve. Such a protective sleeve preferably includes a plurality of holes spaced along a major surface area of the protective sleeve.

The method may further include the chronological steps of: providing and fluidly communicating a lubricant dispensing unit with the protective sleeve; reducing friction between the outer surface of the medicine delivering tube and the inner surface of the protective sleeve by injecting lubricant into the lubricant receiving zone; and reducing friction along an outer surface of the protective sleeve by applying an external force to the protective sleeve and causing the lubricant to egress the protective sleeve via the holes.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the disclosure of the application, which is measured by the claims, nor is it intended to be limiting as to the scope of the disclosure in any way.

BRIEF DESCRIPTION OF THE SEVERAL VIEWS OF THE DRAWING

The novel features believed to be characteristic of this disclosure are set forth with particularity in the appended claims. The disclosure itself, however, both as to its organization and method of operation, together with further objects and advantages thereof, may best be understood by reference to the following description taken in connection with the accompanying drawings in which:

FIG. 3 is a schematic diagram showing a lubricant dispensing unit in fluid communication with the protective sleeve;

Figure 1:
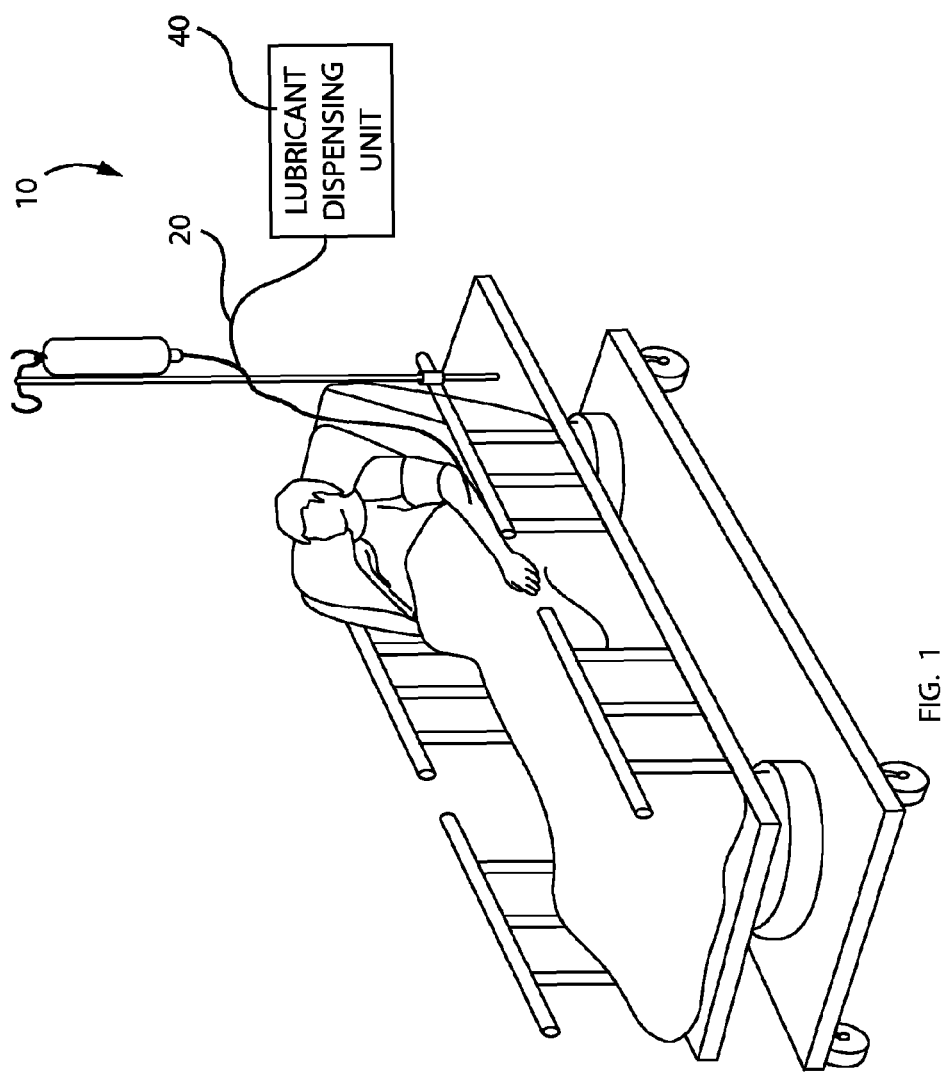
FIG. 1 is a perspective view showing a medicinal tube lubricating system employed in a hospital environment, in accordance with a non-limiting exemplary embodiment of the present disclosure.

Those skilled in the art will appreciate that the figures are not intended to be drawn to any particular scale; nor are the figures intended to illustrate every embodiment of the disclosure. The disclosure is not limited to the exemplary embodiments depicted in the figures or the shapes, relative sizes or proportions shown in the figures.

DETAILED DESCRIPTION OF THE DISCLOSURE

The non-limiting exemplary embodiments will now be described more fully hereinafter with reference to the accompanying drawings, in which a preferred embodiment of the disclosure is shown. This disclosure may, however, be embodied in many different forms and should not be construed as limited to the embodiment set forth herein. Rather, this embodiment is provided so that this application will be thorough and complete, and will fully convey the true scope of the disclosure to those skilled in the art. Like numbers refer to like elements throughout the figures.

The illustrations of the embodiments described herein are intended to provide a general understanding of the structure of the various embodiments. The illustrations are not intended to serve as a complete description of all of the elements and features of system and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

One or more embodiments of the disclosure may be referred to herein, individually and/or collectively, by the term "non-limiting exemplary embodiments" merely for convenience and without intending to voluntarily limit the scope of this application to any particular disclosure or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The below disclosed subject matter is to be considered illustrative, and not restrictive, and the appended claims are intended to cover all such modifications, enhancements, and other embodiments which fall within the true scope of the non-limiting exemplary embodiments. Thus, to the maximum extent allowed by law, the scope of the non-limiting exemplary embodiments is to be determined by the broadest permissible interpretation of the following claims and their equivalents, and shall not be restricted or limited by the foregoing detailed description.

References in the specification to "one embodiment", "an embodiment", "a preferred embodiment", "an alternative embodiment" and similar phrases mean that a particular feature, structure, or characteristic described in connection with the embodiment is included in at least an embodiment of the disclosure. The appearances of the phrase "non-limiting exemplary embodiment" in various places in the specification are not necessarily all meant to refer to the same embodiment.

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiments and are not necessarily intended to be construed as limiting.

Figure 2:
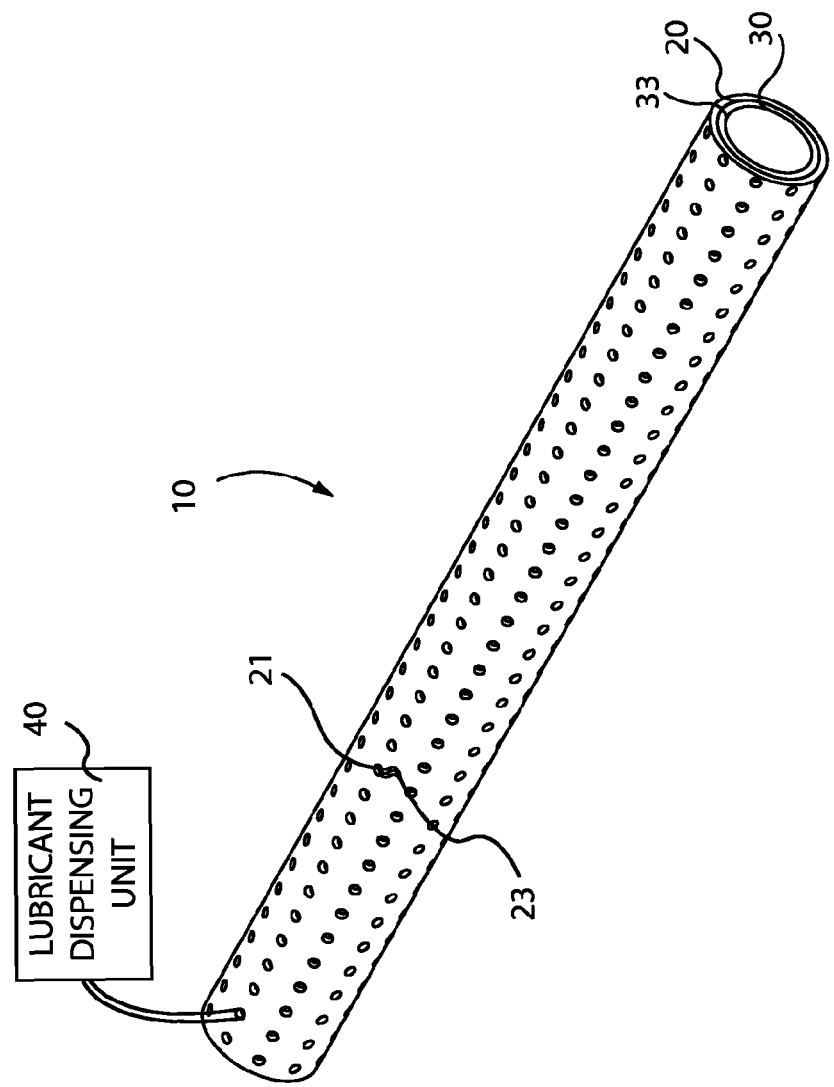
FIG. 2 is an enlarged perspective view showing a protective sleeve positioned about the medicine delivering tube of FIG. 1.
Figure 4A:
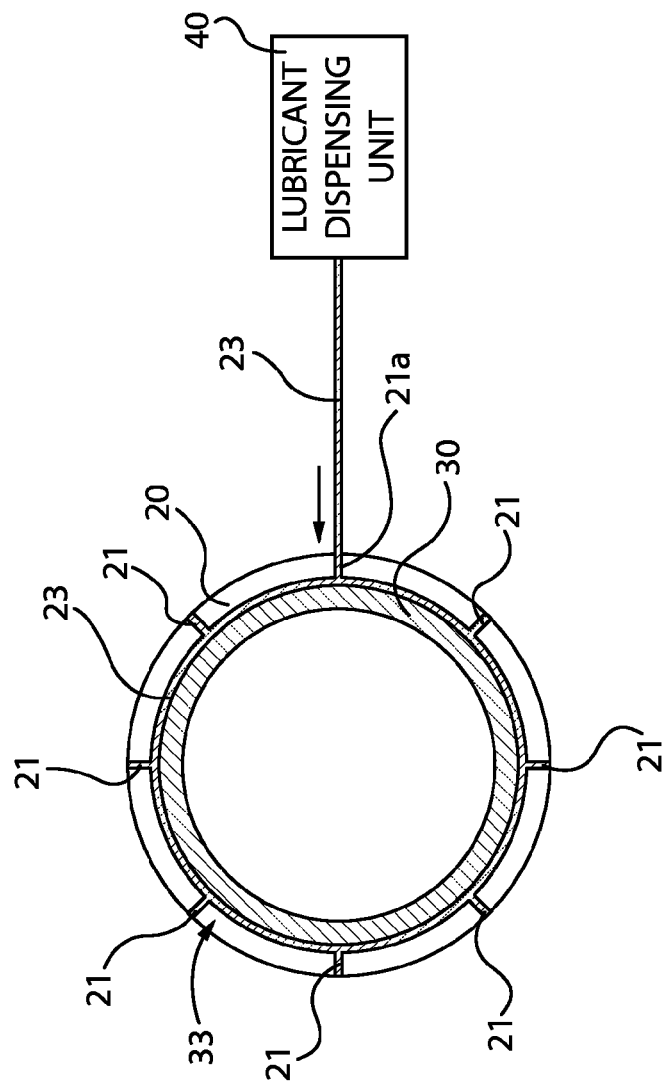
FIG. 4A is an enlarged cross-sectional view taken along line 4-4, illustrating the lubricant receiving zone intercalated between the medicine delivering tube and protective sleeve wherein lubricant is introduced into the lubricant receiving zone.
Figure 4B:
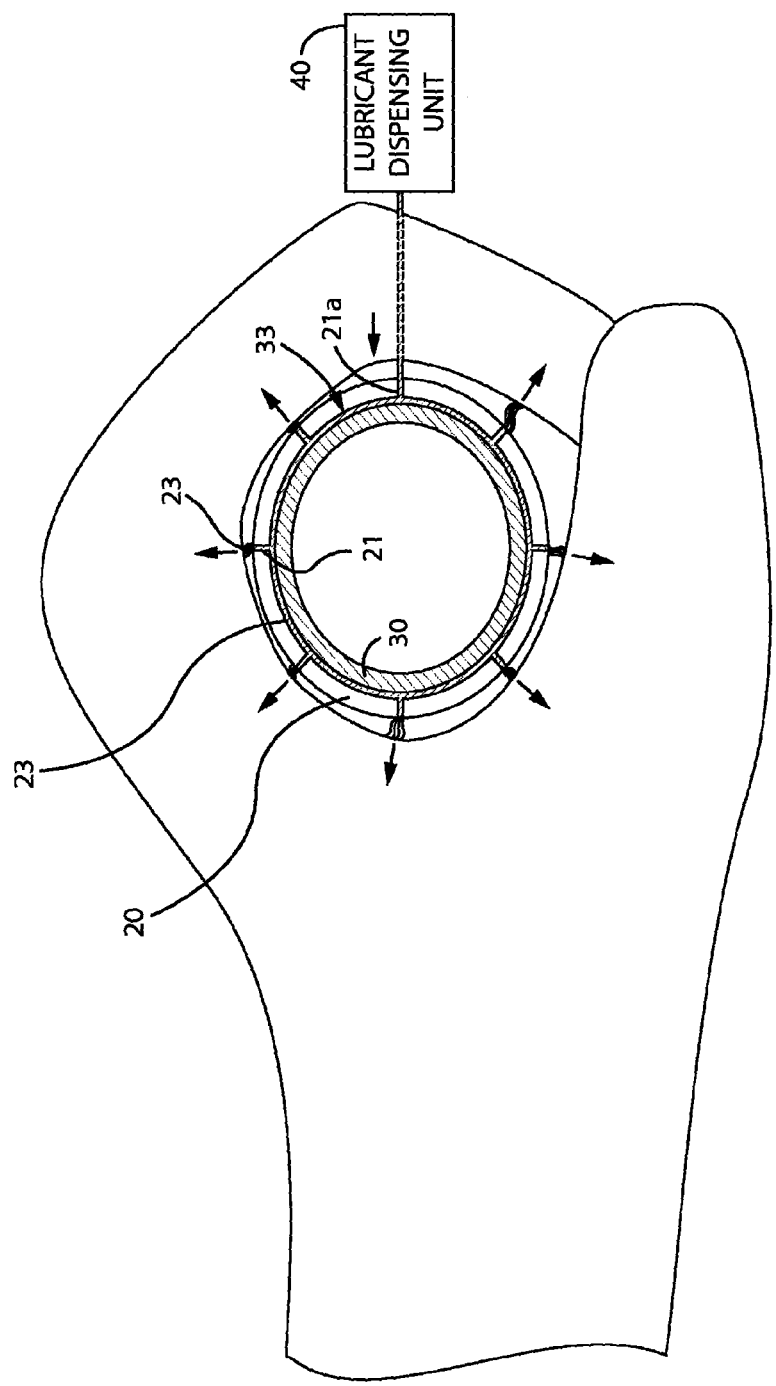
FIG. 4B illustrates an external force applied to the protective sleeve thereby causing lubricant to egress the holes.

The system of this disclosure is referred to generally in FIGS. 1-4B and is intended to provide a medicinal tube 30 lubricating system 10. It should be understood that the present disclosure may be used to prevent patients from accidentally or purposefully pulling out an intravenous and/or nasogastric (IV/NG) tube (medicine delivering tube 30) in many different types of medical and other situations, and should not be limited to the uses described herein.

Referring to FIGS. 1-4B in general, in a non-limiting exemplary embodiment, the medicinal tube lubricating system 10 includes a medicine delivering tube 30 (IV/NG tube) capable of transporting fluid (i.e., blood, medicine) from an existing medicine dispensing unit 40 to the patient. A protective sleeve 20 may be concentrically positioned about an entire longitudinal length of the medicine delivering tube 30 such that a lubricant receiving zone 33 is intercalated between an outer surface of the medicine delivering tube 30 and an inner surface of the protective sleeve 20. The protective sleeve 20 preferably includes a plurality of holes 21 spaced along a major surface area of the protective sleeve 20.

A lubricant dispensing unit 40 is in fluid communication with the protective sleeve 20 thereby injecting lubricant 23 into the lubricant receiving zone 33 for reducing friction between the outer surface of the medicine delivering tube 30 and the inner surface of the protective sleeve 20. Exemplary lubricants may include water-based lubricants 23 as well as oil-based lubricants. Of course, unit 40 may be actuated via a pump to assist in lubricant transfer along protective sleeve 20.

In a non-limiting exemplary embodiment, lubricant 23 may include various agents for spreading, water retention, and resistance to contamination, as well known by one skilled in the relevant art(s). A viscosity of lubricant 23 may be calibrated by adjusting its water/oil content and concentration of cellulose (or other suitable gel-forming hydrophilic ingredient). If lubricant 23 has a tendency to dry out during extended exposure to air, reapplication of lubricant 23 or application of water thereto is sufficient to re-activate the viscosity. In this manner, upon applying an external force to protective sleeve 20, lubricant 23 is caused to egress protective sleeve 20 via holes 21 thereby reducing friction along an outer surface of protective sleeve 20. Such a structural configuration provides the unexpected and unpredictable advantage of prohibiting accidental/intentional dislodge of tube 30 from the patient because the outer surface of protective sleeve 20 and surface contact with tube 30 is too slick for maintaining a grip.

As a result, the system 10 would ensure that patients continuously receive the medication they need. Importantly, such a system 10 may eliminate the need for medical personnel to constantly re-insert tube 30, which is a frustrating endeavor that ends up costing the hospital and the patient money due to delayed procedures.

In a non-limiting exemplary embodiment, lubricant receiving zone 33 continuously extends about an uninterrupted curvilinear path extending along an entire circumference of the outer surface of the medicine delivering tube 30. Such a structural configuration provides the unexpected and unpredictable advantage of prohibiting frictional engagement between any portion of protective sleeve 20 and tube 20.

In a non-limiting exemplary embodiment, lubricant 23 maintains continuous contact with the outer surface of the medicinal delivering tube 30 and the inner surface of the protective sleeve 20 prior to egressing from the holes 21. Such a structural configuration provides the unexpected and unpredictable advantage of adequate reduction in friction contact between sleeve 30 and tube 20.

In a non-limiting exemplary embodiment, holes 21 pass through an entire cross-section of protective sleeve 20 thereby extending from the lubricant receiving zone 33 and terminating at the outer surface of the protective sleeve 20. Such a structural configuration provides the unexpected and unpredictable advantage of ensuring lubricant 23 effectively exits out of protective sleeve 20 and lubricates an outer surface thereof.

In a non-limiting exemplary embodiment, lubricant 23 simultaneously ingresses lubricant receiving zone 33 via one hole 21a and egresses from the remaining holes 21. Such a structural configuration provides the unexpected and unpredictable advantage of permitting a caregiver to ingress/egress lubricant 23 from protective sleeve 20 without creating a pressurized bubble between sleeve 20 and tube 30.

In a non-limiting exemplary embodiment, lubricant 23 is prohibited from entering an interior of tube 30. Such a structural configuration provides the unexpected and unpredictable advantage of avoiding contamination of medicine passing through tube 30.

In a non-limiting exemplary embodiment, holes 21 are radially oriented and equidistantly spaced from a center of medicine delivering tube 30. Such a structural configuration provides the unexpected and unpredictable advantage of ensuring lubricant 23 is evenly dispersed out from sleeve 20 thereby covering the outer surface thereof.

The present disclosure further includes a method of utilizing a medicinal tube lubricating system 10 for ensuring a patient continuously receives medication during an extended time period. Such a method preferably includes the chronological steps of: providing a medicine delivering tube 30 and an existing medicine dispensing unit 40 wherein the medicine delivering tube 30 is capable of transporting fluid from the existing medicine dispensing unit 40 to the patient; and providing and concentrically positioning a protective sleeve 20 about an entire longitudinal length of the medicine delivering tube 30 such that a lubricant receiving zone 33 is formed between an outer surface of the medicine delivering tube 30 and an inner surface of the protective sleeve 20. Such a protective sleeve 20 preferably includes a plurality of holes 21 spaced along a major surface area of the protective sleeve 20.

The method may further include the chronological steps of: providing and fluidly communicating a lubricant dispensing unit 40 with protective sleeve 20; reducing friction between the outer surface of medicine delivering tube 30 and the inner surface of protective sleeve 20 by injecting lubricant 23 into the lubricant receiving zone 33; and reducing friction along an outer surface of protective sleeve 20 by applying an external force to protective sleeve 20 and causing the lubricant 23 to egress protective sleeve 20 via holes 21. Such a structural configuration provides the unexpected and unpredictable advantage of prohibiting accidental/intentional dislodge of tube 30 from the patient because the outer surface of protective sleeve 20 and surface contact with tube 30 is too slick for maintaining a grip.

In a non-limiting exemplary embodiment, tube 30 may be attached to the patient's nose or body as desired and the system 10 may work by dispensing lubricant 23 out of egress holes 21 of sleeve 20 whenever the patient pulls on them. In this way, sleeve 20 and tube 30 become too slick for the patient to gain traction, and thus remain connected to the patient.

While the disclosure has been described with respect to a certain specific embodiment, it will be appreciated that many modifications and changes may be made by those skilled in the art without departing from the spirit of the disclosure. It is intended, therefore, by the appended claims to cover all such modifications and changes as fall within the true spirit and scope of the disclosure. In particular, with respect to the above description, it is to be realized that the optimum dimensional relationships for the parts of the non-limiting exemplary embodiments may include variations in size, materials, shape, form, function and manner of operation.

What is claimed as new and what is desired to secure by Letters Patent of the United States is:

1. A method of utilizing a medicinal tube lubricating system for ensuring a patient continuously receives medication during an extended time period, said method comprising the chronological steps of:

providing a medicine delivering tube and an existing medicine dispensing unit, said medicine delivering tube being capable of transporting fluid from the existing medicine dispensing unit to the patient;

providing and concentrically positioning a protective sleeve about an entire longitudinal length of said medicine delivering tube such that a lubricant receiving zone is intercalated between an outer surface of said medicine delivering tube and an inner surface of said protective sleeve, said protective sleeve including a plurality of holes spaced along a major surface area of said protective sleeve;

providing and fluidly communicating a lubricant dispensing unit with said protective sleeve;

reducing friction between said outer surface of said medicine delivering tube and said inner surface of said protective sleeve by injecting lubricant into said lubricant receiving zone; and reducing friction along an outer surface of said protective sleeve by applying an external force to said protective sleeve and causing said lubricant to egress said protective sleeve via said holes.

\* \* \* \* \*